United States Patent
Fisher et al.

(10) Patent No.: US 11,464,414 B2
(45) Date of Patent: Oct. 11, 2022

(54) NON-INVASIVE CARDIAC OUTPUT DETERMINATION

(71) Applicant: THORNHILL SCIENTIFIC INC., Toronto (CA)

(72) Inventors: Joseph Fisher, Thornhill (CA); Michael Klein, Toronto (CA); James Duffin, Toronto (CA)

(73) Assignee: THORNHILL SCIENTIFIC INC., North York (CA)

( * ) Notice: Subject to any disclaimer, the term of this patent is extended or adjusted under 35 U.S.C. 154(b) by 444 days.

(21) Appl. No.: 16/503,866

(22) Filed: Jul. 5, 2019

(65) Prior Publication Data

US 2020/0069194 A1 Mar. 5, 2020

Related U.S. Application Data

(63) Continuation of application No. 15/945,436, filed on Apr. 4, 2018, now abandoned, which is a continuation
(Continued)

(51) Int. Cl.
*A61B 5/0205* (2006.01)
*A61B 5/00* (2006.01)
(Continued)

(52) U.S. Cl.
CPC ........... *A61B 5/0205* (2013.01); *A61B 5/026* (2013.01); *A61B 5/029* (2013.01); *A61B 5/0813* (2013.01);
(Continued)

(58) Field of Classification Search
CPC ......... A61B 5/0205; A61B 5/00; A61B 5/026; A61B 5/029; A61B 5/08; A61B 5/083;
(Continued)

(56) References Cited

U.S. PATENT DOCUMENTS

| | | | | |
|---|---|---|---|---|
| 4,947,860 A | * | 8/1990 | Fisher | G01N 33/4925 600/532 |
| 7,070,569 B2 | * | 7/2006 | Heinonen | A61B 5/029 600/484 |
| 2009/0120435 A1 | * | 5/2009 | Slessarev | A61M 16/0051 128/203.14 |

OTHER PUBLICATIONS

Peyton et al., "Non-invasive automated measurement of cardiac output during stable cardiac surgery using a fully integrated differential CO2 Fick method," J. Clin. Mon. & Comput., 22:285-292 (2008) (Year: 2008).*

* cited by examiner

*Primary Examiner* — Eric J Messersmith
(74) *Attorney, Agent, or Firm* — Perry + Currier Inc.

(57) ABSTRACT

A method of controlling a gas delivery apparatus including an apparatus controllable variable using an iterative algorithm to deliver a test gas (TG) for non-invasively determining a subject's pulmonary blood flow comprising iteratively generating and evaluating test values of a iterated variable based on an iterative algorithm in order output a test value of the iterated variable that meets a test criterion wherein iterative algorithm is characterized in that it defines a test mathematical relationship between the at least one apparatus controllable variable, the iterated variable and an end tidal concentration of test gas attained by setting the apparatus controllable variable, such that the iterative algorithm is determinative of whether iteration on the test value satisfies a test criterion or iteratively generates a progressively refined test value.

20 Claims, 4 Drawing Sheets

Related U.S. Application Data of application No. 15/438,503, filed on Feb. 21, 2017, now abandoned, which is a continuation of application No. 13/697,768, filed as application No. PCT/CN2011/000577 on May 18, 2011, now abandoned.

(60) Provisional application No. 61/345,952, filed on May 18, 2010.

(51) Int. Cl.
| | |
|---|---|
| *A61B 5/029* | (2006.01) |
| *A61B 5/083* | (2006.01) |
| *A61B 5/08* | (2006.01) |
| *A61B 5/026* | (2006.01) |
| *A61M 16/00* | (2006.01) |
| *A61M 16/12* | (2006.01) |

(52) U.S. Cl.
CPC .......... *A61B 5/0836* (2013.01); *A61B 5/7225* (2013.01); *A61B 5/7278* (2013.01); *A61M 16/0057* (2013.01); *A61M 16/12* (2013.01); *A61B 5/082* (2013.01)

(58) Field of Classification Search
CPC ... A61B 5/7278; A61B 5/0813; A61B 5/0836; A61B 5/7225; A61B 5/082; A61M 16/00; A61M 16/12; A61M 16/0057
See application file for complete search history.

NON-INVASIVE CARDIAC OUTPUT DETERMINATION

CROSS-REFERENCE TO RELATED APPLICATION

This application is a Continuation of U.S. application Ser. No. 13/697,768, filed Jan. 16, 2013, which is national phase filing, under 35 U.S.C. § 371(c), of International Application No. PCT/CA2011/000577, filed May 18, 2011, the disclosures of which are incorporated herein by reference in their entireties. International Application No. PCT/CA2011/000577, in turn, claims the benefit, under 35 U.S.C. § 119(e), of U.S. provisional application Ser. No. 61/345,952, filed on May 18, 2010, the disclosure of which is incorporated herein by reference in its entirety.

FIELD OF THE INVENTION

The present invention relates to a novel method for non-invasively measuring pulmonary blood flow, to a novel method for controlling a gas delivery apparatus and to a system and apparatus for implementing the methods.

BACKGROUND OF THE INVENTION

Many methods have been developed which attempt to measure pulmonary blood flow without invasive access to the circulation ($\dot{Q}$). These methods, and their corresponding limitations, have been exhaustively reviewed in the literature [1]. What emerges from these reviews, however, are the potential benefits of non-invasive pulmonary blood flow monitoring and the current lack of an adequate method.

Fick described the relationship between the blood gas concentrations and the minute volume of expired gases during steady state [2]. Specifically, if the amount of $CO_2$ in the lung is not changing, the flux of $CO_2$ between the pulmonary capillary blood and the alveolar space is equal to the minute volume of expired $CO_2$ ($\dot{V}CO_2$). The flux of $CO_2$ between the blood and the lungs can be calculated from the product of the pulmonary blood flow and the difference between the $CO_2$ concentration in the mixed-venous blood ($C\bar{v}CO_2$) entering the pulmonary circulation and the corresponding concentration in the arterialized blood ($CaCO_2$) leaving the pulmonary circulation. The Fick mass balance relation is shown in equation 1.

$$\dot{V}CO_2 = \dot{Q}(C\bar{v}CO_2 - CaCO'_2) \quad \text{(eq. 1)}$$

If the steady state minute volume of expired $CO_2$, arterial $CO_2$ concentration, and mixed-venous $CO_2$ concentration can be determined, then the pulmonary blood flow can be calculated from equation 1. Conventionally, the minute volume of expired $CO_2$ is calculated from bag collection of the expired breath, the product of the minute ventilation and the concentration of $CO_2$ in the mixed-expired gas, or integration of the instantaneous concentration of $CO_2$ at the mouth weighted by the instantaneous flow. The partial pressure of $CO_2$ in the arterial blood is assumed to be equal to the end-tidal partial pressure of $CO_2$ and then converted to a concentration via the $CO_2$ dissociation curve of oxygenated whole blood [3,4]. Traditionally, two methods have been used to estimate the mixed-venous concentration of $CO_2$ for the purpose of pulmonary blood flow measurement. The first method was presented by Defares [5]; the method of Collier [6] was published shortly thereafter.

In the method described by Defares, rebreathing is executed from a bag with a low initial concentration of $CO_2$. As rebreathing proceeds, the level of $CO_2$ in the bag and the lung exponentially approach that in the mixed-venous blood. However, equilibration of the bag and the lung with the mixed-venous blood is slow as the volume of gas in the functional residual capacity is large. As a result, equilibration does not usually occur before the change in the arterial $CO_2$ induced by rebreathing recirculates back to the lung. The steady state mixed-venous $CO_2$—the asymptote of the exponential rise in end-tidal $CO_2$—must therefore be calculated from fitting an exponential curve to the end-tidal $CO_2$ of the breaths during rebreathing prior to recirculation.

In the method introduced by Collier, rebreathing is executed from a bag with an initial concentration of $CO_2$ slightly above an estimated mixed-venous $CO_2$ concentration. The initial $CO_2$ in the bag is intended to, upon inhalation, eliminate the $CO_2$ diffusion gradient between the functional residual capacity and the mixed-venous blood on the first breath of rebreathing. The equilibrium between the mixed-venous blood and the alveolar space is recognized by the presence of a plateau in the end-tidal $CO_2$ during rebreathing.

As a variant of these rebreathing methods, Gedeon described a partial $CO_2$ rebreathing method for measuring pulmonary blood flow [7]. Partial rebreathing differs from the full rebreathing methods of Defares and Collier in that the entire tidal volume is not composed of rebreathed gas. Partial rebreathing is implemented by introducing a serial dead space into the breathing circuit to increase the volume of rebreathed gas in each breath [8].

Partial rebreathing increases the average $CO_2$ content of the inspired gas so that the flux of expired $CO_2$ is reduced. As a result, the alveolar and arterial $CO_2$ concentrations rise towards the level at which the flux of $CO_2$ between the blood and the lung will once again equal the expired flux. Like the method of Defares, equilibration during rebreathing may not occur before recirculation. Nevertheless, the Fick mass balance relation is applied at the end of rebreathing as shown in equation 2.

$$\dot{V}CO'_2 = \dot{Q}(C\bar{v}CO_2 - CaCO'_2) \quad \text{(eq. 2)}$$

Two steady states can be solved for the pulmonary blood flow and the mixed-venous concentration of $CO_2$, revealing the differential Fick equations shown in equations 3a1 and 3b1.

$$\dot{Q} = \frac{\dot{V}CO'_2 - \dot{V}CO_2}{CaCO_2 - CaCO'_2} \quad \text{(eq. 3a1)}$$

$$C\bar{v}CO_2 = \frac{CaCO_2 \cdot \dot{V}CO'_2 - CaCO'_2 \cdot \dot{V}CO_2}{\dot{V}CO'_2 - \dot{V}CO_2} \quad \text{(eq. 3b1)}$$

In practice, fluctuations in alveolar ventilation induce perturbations in the instantaneous flux of expired $CO_2$ and in arterial $CO_2$ levels, leading to significant errors in calculating pulmonary blood flow. This error is pronounced in untrained spontaneous breathers [9].

In the method of Defares specifically, the mixed-venous concentration of $CO_2$ is extrapolated from the exponential rise in the end-tidal $CO_2$ measured during rebreathing before recirculation. However, the number of breaths available for calculating the exponential asymptote is limited, and as a result, determination of the mixed-venous $CO_2$ is highly sensitive to errors in the end-tidal measurements.

Alternatively, in the method of Collier, the mixed-venous $CO_2$ concentration is measured, but equilibration of the lung with the mixed-venous $CO_2$ before recirculation depends on the initial volume and composition of the gas in the rebreathing bag. The optimal starting conditions vary with the subject's mixed-venous concentration of $CO_2$ and functional residual capacity so that, in practise, an effective starting volume and concentration is determined by trial-and-error in repeated executions of the rebreathing manoeuvre until a plateau is observed in the end-tidal record [6].

In partial rebreathing methods, the last breath of the rebreathing phase is assumed to represent the second steady state conditions required to calculate the pulmonary blood flow. However, where the rebreathing period is short, equilibrium is not achieved; and, where the rebreathing period is long recirculation confounds the measurement [10].

Therefore, although measuring pulmonary blood flow (Q) should be an integral part of clinical monitoring and physiological research, it is not routinely implemented because of the invasiveness, cost, or inaccuracy of existing methods. To be of the greatest utility, a pulmonary blood flow monitor must provide accurate, rapid, and repeatable measurements over a broad range of physiological and pathological conditions.

SUMMARY OF THE INVENTION

We have developed a novel system for non-invasively measuring the pulmonary blood flow that implements an iterative respiratory algorithm and thereby overcomes the limitations of previous methods. The method can be adapted to an automated system for non-invasively measuring pulmonary blood flow that provides for reliable monitoring of pulmonary blood flow in a wide range of subjects and environments. According to one aspect, the invention is directed to a method of controlling a gas delivery apparatus to deliver a test gas (TG) for non-invasively determining a subject's pulmonary blood flow comprising the steps of:

(a) Controlling at least one apparatus controllable variable to test one or more test values for an iterated variable in an iterative algorithm by:
   A) providing an inspired concentration of a test gas that achieves a test concentration of the test gas in the subject's end tidal exhaled gas;
   B) using a test value of an iterated variable in an iterative algorithm to set the gas delivery apparatus to deliver, for at least one series of inspiratory cycles, an inspiratory gas comprising a test gas that is computed to target the test concentration of the test gas based on a test value of the iterated variable;
   C) obtaining input comprising measurements of a measurable variable for at least one series of inspiratory cycles, optionally end tidal concentrations of test gas for expiratory cycles corresponding to the at least one series of inspiratory cycles;
   D) using at least one measurement obtained in step C) as a reference end tidal concentration value to generate at least one of the following outputs:
      (1) a test value satisfies the test criterion;
      (2) a refined test value;
      wherein the reference end tidal concentration is a surrogate steady state value and is used to generate the refined test value;

(b) If output (1) is not obtained, repeating step (a) as necessary at least until output (1) is obtained; and (c) If output (1) is obtained, outputting a value for pulmonary blood flow which, based on the test criterion, sufficiently represents a subject's true pulmonary blood flow.

As described below, obtaining steady state values for at least one apparatus controllable variable and an end tidal concentration of test gas for or as part of the test is central to exploiting key test mathematical relationships that may be employed in the iterative algorithm. The rate of flow of inspiratory gas into the breathing circuit, when determinative of alveolar ventilation can be used to compute a minute volume of expired test gas. A variety of other non-invasive or invasive ways of obtaining these values are known. These values may conveniently be resting steady state values. Therefore, while it is not necessary to employ the invention to obtain these values, they are employed in the execution of the iterative algorithm or for the algorithm. Hence, according to a preferred embodiment of the invention, initial steady state values are obtained within or for the iterative algorithm. For convenience, this stage of gathering input of steady state values for the iterative algorithm is referred to as the baseline phase.

According to another aspect, the invention is directed to a method for non-invasively determining pulmonary blood flow comprising obtaining steady state values for minute volume of expired test gas and end tidal concentration of test gas and implementing steps (a) to (c) as defined above, the method adapted to be implemented by a gas delivery apparatus as defined herein. The method can be executed rapidly and is non-therapeutic in nature. The method may be carried out as a preliminary step to obtaining a diagnosis in which obtaining pulmonary blood flow is useful for the ensuing diagnosis or forms part of a broader diagnostic work-up.

According to yet another aspect, the invention is directed to a gas delivery system adapted to deliver a test gas (TG) for non-invasively determining a subject's pulmonary blood flow comprising:

A gas delivery apparatus;

A control system for controlling the gas delivery apparatus based on an iterative algorithm including controlling at least one apparatus controllable variable to test one or more test values for an iterated variable, the control system comprising a computer, the gas delivery system including means for:
   A) Obtaining input of steady state values sufficient for input into the differential Fick equation, optionally minute volume of expired test gas and an end tidal concentration of test gas;
   B) Obtaining input of a test concentration of the test gas in the subject's end tidal exhaled gas wherein the test concentration of test gas is achieved by administration of a test gas bolus;
   C) Using a test value of the iterated variable in an iterative algorithm to set a gas delivery apparatus to deliver, for at least one series of inspiratory cycles, a test gas that is computed to maintain the test concentration of the test gas;
   D) Obtaining input comprising measurements of end tidal concentrations of test gas for expiratory cycles corresponding to the at least one series of inspiratory cycles;
   E) using at least one measurement obtained in step D) as a reference end tidal concentration value to generate at least one of the following outputs:
      (1) the test value satisfies the test criterion;
      (2) a refined test value;
      wherein the reference end tidal concentration is a surrogate steady state value and is used to generate the refined test value;
wherein the control system is adapted to iteratively test a series of test values for the iterated variable based on the following criteria:

If output (1) is not obtained, repeating step (B) to (E) as necessary at least until output (1) is obtained; and If output (1) is obtained, outputting a value for pulmonary blood flow which, based on the test criterion, sufficiently represents a subject's true pulmonary blood flow.

The computer, as broadly defined herein is understood to supply all the necessary components that are not contained with the gas delivery apparatus. Optionally, a separate CPU runs program code used to control a gas delivery apparatus comprising one or more conventional components of a gas blender. The gas delivery apparatus may be operatively connected to one or more gas analyzers including a gas analyzer for the test gas. The gas delivery apparatus is optionally operatively associated with a pressure transducer as described below. The computer receives inputs from one or more input devices for inputting values for various test parameters and values described herein and inputs from the gas analyzer and pressure transducer and provide outputs to suitable flow controllers and a computer readout for example a screen to output of key parameters and values described herein, including preferably a value for pulmonary blood flow.

The iterated variable is preferably pulmonary blood flow and optionally may be an iterated variable determined by pulmonary blood flow from which pulmonary blood flow may be calculated. For example, depending on the choice of test gas, the iterated variable may be the mixed venous concentration of the test gas.

The iterative algorithm is characterized in that it defines a mathematical relationship between the at least one apparatus controllable variable, the iterated variable and a measurable variable, optionally the end tidal concentration attained by setting the apparatus controllable variable, such that the iterative algorithm is determinative of whether iteration on the test value satisfies a test criterion.

The iterative algorithm preferably employs a test mathematical relationship based on the Fick equation and differential Fick equation. The iterative algorithm optionally employs equation 5 or 5-0.

The iterative algorithm may be based on the Fick or differential Fick equation.

The at least one apparatus controllable variable is optionally a controllable inspired concentration of test gas in the inspiratory gas.

The at least one apparatus controllable variable is optionally a controllable rate of flow of test gas-containing inspiratory gas into the breathing circuit such that the rate of flow is indicative of or determinative of the alveolar ventilation, as described below.

The apparatus controllable variable may be both a selectable inspired concentration of test gas in the inspiratory gas and the rate of flow of the inspiratory gas into the breathing circuit For convenience, the apparatus controllable variable is preferably a selectable inspired concentration of test gas in the inspiratory gas which targets the test concentration of test gas in the end tidal gas obviating the need to change the rate of flow of inspiratory gas set for the test.

The iterative algorithm may in one embodiment rely on equation 5 or 5-0 as the test mathematical relationship which is based on the Fick equation to solve for an the inspired concentration of test gas in the inspiratory gas which targets the test concentration of test gas in the end tidal gas. The equation may be equation 7a or 7a-0 as defined below. These equations pertain to $CO_2$ as a test gas but may be generalized to another test gas. Inputs in equation 7a and 7a-0 may be obtained from equations 6a and 6b, and 6a-0/6b-0, respectively, which may also be generalized to another test gas where the relationship between end tidal and arterial values is established or readily ascertained.

The iterative algorithm may rely on equation 5 or 5-0 to solve for a rate of flow of inspiratory gas into the breathing circuit which targets the test concentration of test gas in the end tidal gas. The equation may be equation 7b or 7b-0 as defined below. These equations pertain to $CO_2$ as a test gas but may be generalized to another test gas where the relationship between end tidal and arterial values is established or readily ascertained. Inputs in equation 7b and 7b-0 may be obtained from equations 6a and 6b, and 6a-0/6b-0, respectively, which may also be generalized to another test gas where the relationship between end tidal and arterial values is established or readily ascertained.

The at least one apparatus controllable variable is optionally the rate of flow of test gas-containing inspiratory gas into the breathing circuit such that the rate of flow is determinative and reliably indicative of the alveolar ventilation. For example, the alveolar ventilation of a subject that is paralyzed and not making an independent inspiratory effort may be controlled by a ventilator setting.

Preferably the rate of flow of test gas-containing inspiratory gas into the breathing circuit is determinative of the alveolar ventilation, optionally wherein the fresh gas flow is set to be equal to or less than the minute ventilation and the balance of the subject's inspiratory requirements are made up by a neutral gas, [11] for example re-breathed gas.

Optionally, the breathing circuit is a sequential gas delivery circuit which allows a subject to re-breath expired end tidal gas when the flow of gas into the breathing circuit is set to be equal to or less than the minute ventilation. The circuit may organize passive access to the rebreathed gas. The flow of gas may be set to fill an inspiratory reservoir which the subject can then deplete in each inspiratory cycle, whereupon negative pressure in the circuit triggers access to a re-breathed gas until the end of inspiration.

Optionally, the refined test value is ascertained based on the differential Fick equation (eq. 3a1 or 3b1), by using steady state values of VCO2 and CaCO2, optionally resting steady state values obtained prior to establishing a test concentration of test gas in the end tidal gas. These values are important inputs into other equations as well. In this manner, the reference end tidal concentration is used to generate a refined test value for the iterated variable. Alternatively, the estimate can be refined based on an estimate obtained using equations 3a2 or 3b2 as described below.

The "test concentration" of the test gas is the arterial concentration of test gas following administration a test gas bolus as reflected in the end tidal gas following the inspiratory cycle in which the test gas bolus is administered. A test gas bolus is one which achieves a physiologically compatible test concentration of the test gas in the arterial circulation, and increases the concentration of the test gas sufficiently to make the iterative testing of test values (one or more successive test values) accurate having regard to the test criterion and the speed/accuracy of the gas delivery apparatus and gas sensor used to measure the end tidal concentration values. Optionally, when using a sequential gas delivery circuit to perform the test, a test concentration of test gas may be administered by reducing the inspiratory flow in a manner (e.g. setting the flow to 0 for one breath) in which the test gas bolus is constituted by exhaled gas, for example, where the test gas is carbon dioxide a gas having a higher concentration of carbon dioxide.

The test criterion optionally serves to define an acceptable difference between the reference end tidal concentration of test gas and the test concentration of test gas, which establishes that a test value or a refined test value is acceptably close to a value from which the true pulmonary blood flow can be ascertained. The test criterion may also be to iterate a defined number of times. The test criterion may be to continue the iteration indefinitely by fixing this outcome (e.g. by determining that satisfaction of the test criterion is false).

Therefore, according to one embodiment, the invention is directed to a method of controlling a gas delivery apparatus to deliver a test gas (TG) for non-invasively determining a subject's pulmonary blood flow comprising the steps of:

(a) Controlling the flow of an inspiratory gas comprising a test gas into a breathing circuit, wherein the concentration of the test gas in the inspiratory gas ($FiTG_{gi}$) or the rate of flow of gas into the circuit is adjusted to test one or more test values for a iterated variable selected from the group comprising pulmonary blood flow or mixed venous test gas concentration ($C\bar{v}TG$) by:

A) obtaining input of a steady state end tidal concentration and at least one corresponding apparatus controllable variable B) providing an inspired concentration of a test gas that achieves a test concentration of the test gas in the subject's end tidal exhaled gas;

C) using a test value of an iterated variable in a test mathematical relationship to set the gas delivery apparatus to deliver, for at least one series of inspiratory cycles, a test gas that is computed to maintain the test concentration of the test gas;

D) obtaining input comprising measurements of end tidal concentrations of test gas for expiratory cycles corresponding to the at least one series of inspiratory cycles;

E) using at least one measurement obtained in step D) as a reference end tidal concentration value to generate at least one of the following outputs:
(1) the test value satisfies the test criterion;
(2) a refined test value, wherein the reference end tidal concentration is a surrogate steady state value and is used to generate the refined test value;

(b) If output (a) is not obtained, repeating step (a) as necessary until output (1) is obtained; and (c) If output (1) is obtained, outputting a value for pulmonary blood flow which, based on the test criterion, that sufficiently represents a subject's true pulmonary blood flow.

Optionally, the reference end tidal concentration is the last end tidal concentration value obtained prior to a recirculation or an average of the last end tidal concentration values.

According to another aspect, the invention is directed to a method for non-invasively determining a subject's pulmonary blood flow comprising the steps of:

(a) Controlling the flow of an inspiratory gas comprising a test gas into a breathing circuit, wherein the concentration of the test gas in the inspiratory gas ($FiTG_{gi}$) or the rate of flow of gas into the circuit is adjusted to test one or more test values for a iterated variable selected from the group comprising pulmonary blood flow or mixed venous test gas concentration ($C\bar{v}TG$) by:

A) obtaining input of a steady state end tidal concentration and a corresponding value of at least one apparatus controllable variable;

B) providing an inspired concentration of a test gas that achieves s a test concentration of the test gas in the subject's end tidal exhaled gas;

C) using a test value of an iterated variable in a test mathematical relationship to set the gas delivery apparatus to deliver, for at least one series of inspiratory cycles, a test gas that is computed to maintain the test concentration of the test gas;

D) obtaining input comprising measurements of end tidal concentrations of test gas for expiratory cycles corresponding to the at least one series of inspiratory cycles;

E) using at least one measurement obtained in step C) as a reference end tidal concentration value to generate at least one of the following outputs:
(3) the test value satisfies the test criterion;
(4) a refined test value, wherein the reference end tidal concentration is a surrogate steady state value and is used to generate the refined test value;

(b) If output (a) is not obtained, repeating step (a) as necessary until output (1) is obtained; and (c) If output (1) is obtained, outputting a value for pulmonary blood flow which, based on the test criterion, that sufficiently represents a subject's true pulmonary blood flow.

According to optional embodiments of a method as defined above:

1. the test gas is carbon dioxide;
2. a subject's consumption of the test gas containing inspiratory gas is controlled to define the subject's alveolar ventilation (the minute volume of gas which reaches the alveoli and may participate in gas exchange).
3. the subject's alveolar ventilation is defined by setting the rate of flow of a test gas containing gas into a breathing circuit to be equal to or less than the subject's minute ventilation and delivering to the subject on inspiration, the test gas containing inspiratory gas and when the test gas is depleted for a breath, for the balance of that breath, a neutral (for example rebreathed) gas.

According to another aspect the invention is directed to an inspiratory gas delivery system for non-invasively determining pulmonary blood flow comprising:

(a) A gas delivery apparatus;
(b) A control system for controlling the gas delivery apparatus including:

Means for obtaining input of:
a. a steady state value of an end tidal concentration of a test gas and a corresponding value for at least one apparatus controllable variable;
b. a test concentration of a test gas in the subject's end tidal gas;
c. test value for an iterated variable for input into an iterative algorithm;
d. a test criterion;
e. a reference end tidal concentration representing a surrogate steady state value;

Means for computing:
f. a value for at least one apparatus controllable variable, said value computed by the iterative algorithm to maintain the test concentration of test gas in the subject's end tidal gas for a series of inspiratory cycles, the reference end tidal concentration selected or computed from selected measurements of end tidal concentrations of test gas for expiratory cycles corresponding to the at least one series of inspiratory cycles;
g. iteratively, where a previously computed test value does not meet the test criterion, until a test criterion is met, a refined test value for a iterated variable and a corresponding value for an apparatus controllable variable generated by the iterative algorithm for an ensuing series of inspiratory cycles so as to provide a new reference end tidal concentration for comparison to the then current reference test concentration; and means for outputting a test value for a iterated variable that meets the test criterion.

Suitable sequential gas delivery circuits and related apparatus information are disclosed WO/2004/073779, WO/2002/089888 and WO/2001/074433.

To compute the apparatus controlled variable required to maintain the test gas concentration in the end-tidal exhaled gas, the following inputs are needed: the test gas concentration in the end-tidal exhaled gas to be maintained, and a steady state end tidal test gas concentration and a corresponding value of at least one apparatus controllable variable. To refine the estimate of the test value, the following inputs are needed: a steady state end tidal test gas concentration and a corresponding value of at least one apparatus controllable variable, and a reference end tidal test gas concentration and a corresponding value of at least one apparatus controllable variable.

DETAILED DESCRIPTION OF THE INVENTION

Figure 1:
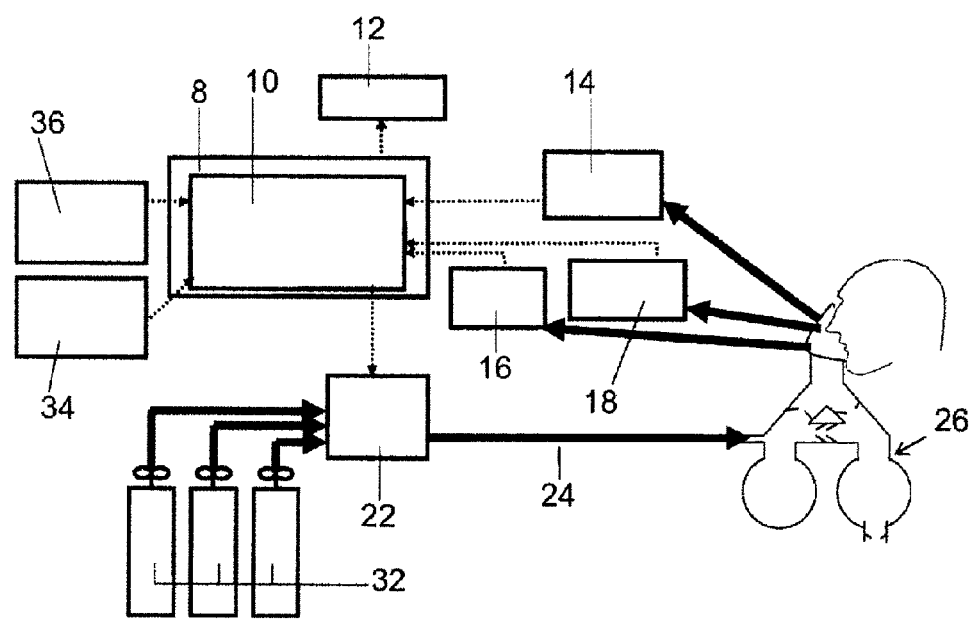
FIG. 1 is a schematic representation of one embodiment of a gas delivery system according to the invention.
Figure 2:
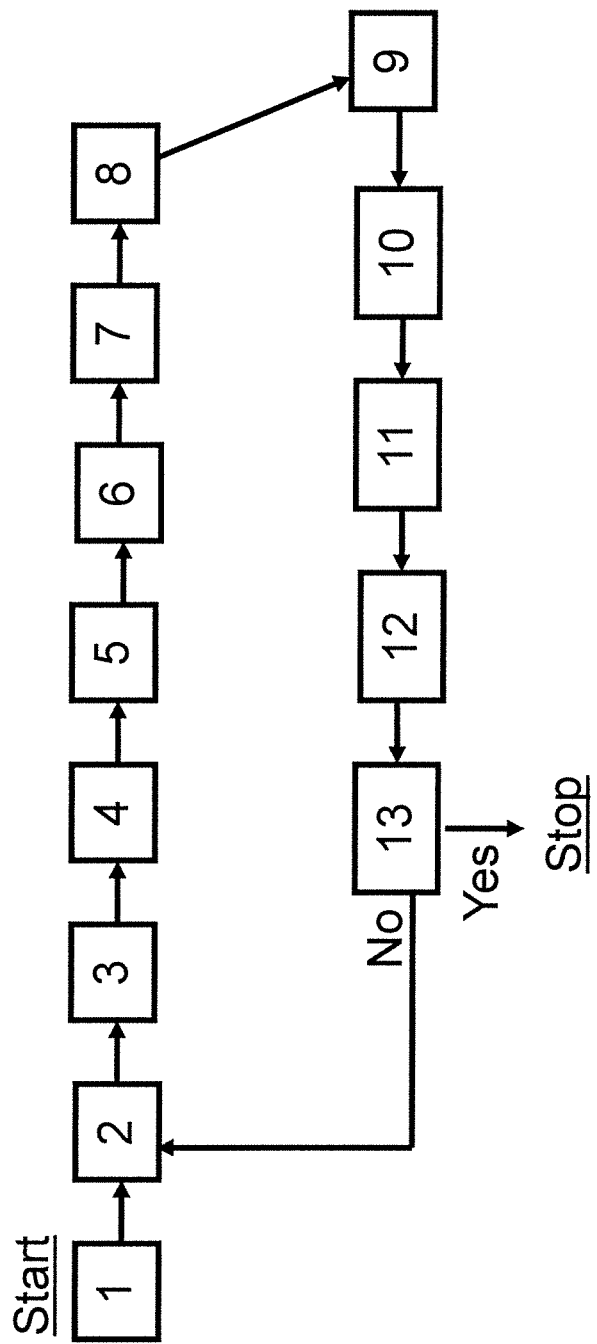
FIG. 2 is a flowchart describing an iterative algorithm employed to recursively determine pulmonary blood flow according to a preferred embodiment of the invention.
Figure 3:
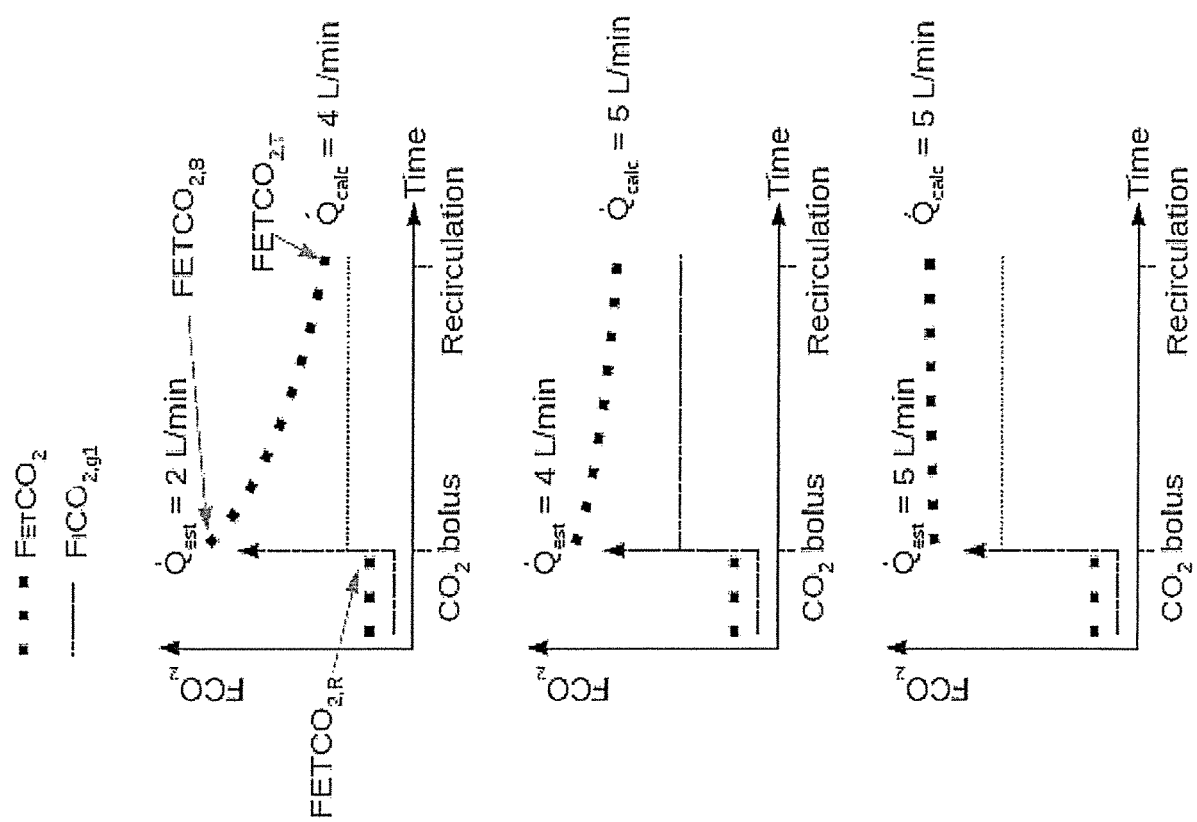
FIG. 3 is a series of a graphical depictions of iterations of the iterative algorithm in which the effect on maintaining a test concentration of test gas for different test values for pulmonary flow is depicted.
Figure 4:
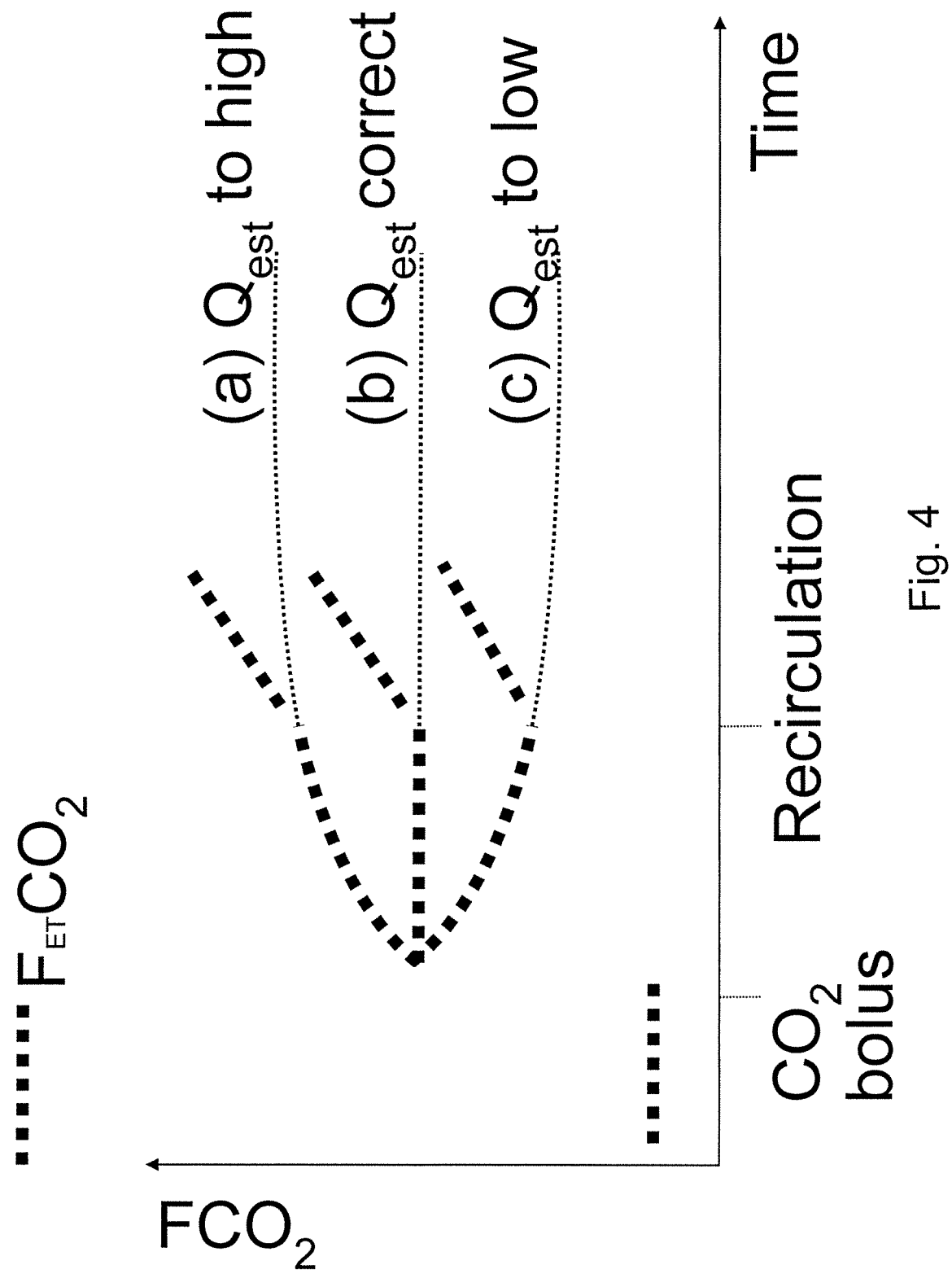
FIG. 4 is a graphical depiction of the effect of over-estimating, under-estimating and correctly estimating a test value for a test variable, in this case, pulmonary blood flow.

Table 1 (below) sets out a list of abbreviations used to express the mathematical relationships employed in the description of several embodiments of the invention described herein.

TABLE 1

| | |
|---|---|
| BSGD | Sequential gas delivery |
| G1 | The gas being supplied to the SGD circuit from a gas blender |
| $\dot{V}_{g1}$ | The flow rate of G1 gas from the gas blender to the SGD circuit |
| Alveolar ventilation | The minute volume of gas that reaches the alveoli and may contribute to gas exchange. Alveolar ventilation = $\dot{V}_{g1}$ when SGD is implemented. |
| $\dot{V}_{g1,R}$ | The flow rate of G1 gas from the gas blender to the SGD circuit throughout the baseline phase |
| $\dot{V}_{g1,T}$ | The flow rate of G1 gas from the gas blender to the SGD circuit throughout the test phase |
| $FICO_{2,g1}$ | Fractional concentration of $CO_2$ in the G1 gas |
| $FIO_{2,g1}$ | Fractional concentration of $O_2$ in the G1 gas |
| $FETCO_2$ | End-tidal fractional concentration of $CO_2$ |
| $FETO_2$ | End-tidal fractional concentration of $O_2$ |
| $CaCO_2$ | Concentration of $CO_2$ in the arterial blood |
| $C\bar{v}CO_2$ | Concentration of $CO_2$ in the mixed-venous blood |
| Q | Pulmonary blood flow |
| $VCO_2$ | Minute volume of expired $CO_2$ |
| $FICO_{2,g1,R}$ | Fractional concentration of $CO_2$ in the G1 gas throughout the baseline phase |
| $FETCO_{2,R}$ | End-tidal fractional concentration of $CO_2$ at the end of the baseline phase |
| $FETO_{2,R}$ | Average end-tidal fractional concentration of $O_2$ during the baseline phase |
| $CaCO_{2,R}$ | Concentration of $CO_2$ in the arterial blood at the end of the baseline phase |
| $VCO_{2,R}$ | Minute volume of expired $CO_2$ at the end of baseline phase |
| $FICO_{2,g1,T}$ | Fractional concentration of $CO_2$ in G1 gas throughout the test phase |
| $FETCO_{2,T}$ | End-tidal fractional concentration of $CO_2$ at the end of the test phase |
| $FETO_{2,T}$ | Average end-tidal fractional concentration of $O_2$ during the test phase |
| $CaCO_{2,T}$ | Concentration of $CO_2$ in the arterial blood at the end of the test phase |
| $VCO_{2,T}$ | Minute volume of expired $CO_2$ at the end of the test phase |
| $FICO_{2,g1,B}$ | Fractional concentration of $CO_2$ in the G1 gas for the bolus breath |
| $FETCO_{2,B}$ | End-tidal fractional concentration of $CO_2$ of the exhalation immediately after inhalation of the bolus |
| $CaCO_{2,B}$ | Concentration of $CO_2$ in the arterial blood immediately after inhalation of the bolus |
| $\dot{Q}_{est}$ | An estimate of pulmonary blood flow used to try and clamp the end-tidal $CO_2$ during the test phase |
| $C\bar{v}CO_{2,est}$ | An estimate of the concentration of $CO_2$ in the mixed-venous blood used to try and clamp the end-tidal $CO_2$ during the test phase |
| $\dot{Q}_{calc}$ | The pulmonary blood flow calculated at the end of the test phase |
| $C\bar{v}CO_{2,calc}$ | The concentration of $CO_2$ in the mixed-venous blood calculated at the end of the test phase |
| $\dot{Q}_{act}$ | The subject's actual pulmonary blood flow |
| $C\bar{v}CO_{2,act}$ | The subject's actual concentration of $CO_2$ in the mixed-venous |
| FRC | Functional residual capacity |
| RR | Respiratory rate |

Table 2 (below) lists the various mathematical relationships employed in the description of embodiments of the invention described herein.

TABLE 2

| Label | Equation | Description |
| --- | --- | --- |
| 1 | $\dot{V}CO_2 = \dot{Q}(C\bar{v}CO_2 - CaCO_2)$ | Fick equation which mathematically expresses the fact that if the end-tidal $CO_2$ is not changing, the minute volume (flux) of expired $CO_2$ is equal to the $CO_2$ deposited in the lung from the circulation |
| 2 | $\dot{V}CO'_2 = \dot{Q}(C\bar{v}CO_2 - CaCO'_2)$ | Fick equation showing that end-tidal and arterial $CO_2$ can be maintained steady at any level for a constant cardiac output and mixed-venous concentration |
| 3a1 | $\dot{Q} = \dfrac{\dot{V}CO'_2 - \dot{V}CO_2}{CaCO_2 - CaCO'_2}$ | If two steady states of end-tidal $CO_2$ can be induced and measured for a constant cardiac output and mixed-venous $CO_2$, (1) and (2) can be solved simultaneously for the cardiac output |
| 3b1 | $C\bar{v}(CO)_2 = \dfrac{CaCO_2 \cdot \dot{V}CO'_2 - CaCO'_2 \cdot \dot{V}CO_2}{\dot{V}CO'_2 - \dot{V}CO_2}$ | If two steady states of end-tidal $CO_2$ can be induced and measured for a constant cardiac output and mixed-venous $CO_2$, (1) and (2) can be solved simultaneously for the mixed-venous $CO_2$ concentration |
| 4 | $\dot{V}CO_2 = \dot{V}_{g1} \cdot \underbrace{\dfrac{310}{293}}_{BTPS} \cdot \left[ \underbrace{\left(\dfrac{1 - FICO_{2,g1} - FIO_{2,g1}}{1 - FETCO_2 - FETO_2}\right)}_{Haldane} \cdot FETCO_2 - FICO_{2,g1} \right]$ | Calculation of the minute volume (flux) of expired CO2 from the end-tidal gases and the flow of gas to a sequential gas delivery circuit |
| 5 | $\dot{V}_{g1} \cdot \dfrac{310}{293} \cdot \left[ \left(\dfrac{1 - FICO_{2,g1} - FIO_{2,g1}}{1 - FETCO_2 - FETO_2}\right) \cdot FETCO_2 - FICO_{2,g1} \right] = \dot{Q}(C\bar{v}CO_2 - CaCO_2)$ | Substitution of (4) for $\dot{V}CO_2$ in (1) |
| 6a | $C\bar{v}CO_2 = \dfrac{\dot{V}_{g1} \cdot \dfrac{310}{293}\left[\left(\dfrac{1 - FICO_{2,g1} - FIO_{2,g1}}{1 - FETCO_2 - FETO_2}\right) \cdot FETCO_2 - FICO_{2,g1}\right]}{\dot{Q}} + CaCO_2$ | Rearrangement of (5) for the mixed-venous CO2 where the end-tidal gases, the flow of gas to a sequential gas delivery circuit, the arterial $CO_2$ concentration, and cardiac output are known or estimated |
| 6b | $\dot{Q} = \dfrac{\dot{V}_{g1} \cdot \dfrac{310}{293} \cdot \left[\left(\dfrac{1 - FICO_{2,g1} - FIO_{2,g1}}{1 - FETCO_2 - FETO_2}\right) \cdot FETCO_2 - FICO_{2,g1}\right]}{C\bar{v}CO_2 - CaCO_2}$ | Rearrangement of (5) for the cardiac output where the end-tidal gases, the flow of gas to a sequential gas delivery circuit, the arterial $CO_2$ concentration, and the mixed-venous $CO_2$ concentration are known or estimated |
| 7a | $FICO_{2,g1} = \dfrac{\dot{V}_{g1} \cdot \dfrac{310}{293} \cdot FETCO_2 \cdot (FIO_{2,g1} - 1) + \dot{Q}(C\bar{v}CO_2 - CaCO_2)(1 - FETO_2 - FETCO_2)}{\dot{V}_{g1} \cdot \dfrac{310}{293} \cdot (FETO_2 - 1)}$ | Rearrangement of (5) for the inspired fraction of $CO_2$ required to maintain end-tidal $CO_2$ at a steady state where the end-tidal gases, the flow of gas to a sequential gas delivery circuit, the arterial $CO_2$ concentration, the mixed-venous $CO_2$ concentration, and cardiac output are known or estimated |
| 7b | $\dot{V}_{g1} = \dfrac{\dot{Q}(C\bar{v}CO_2 - CaCO_2)}{\dfrac{310}{293} \cdot \left[\left(\dfrac{1 - FICO_{2,g1} - FIO_{2,g1}}{1 - FETCO_2 - FETO_2}\right) \cdot FETCO_2 - FICO_{2,g1}\right]}$ | Rearrangement of (5) for the G1 gas flow required to maintain end-tidal $CO_2$ at a steady state where the end-tidal gases, the fractional concentration of $CO_2$ in the G1 gas, the arterial $CO_2$ concentration, the mixed-venous $CO_2$ concentration, and cardiac output are known or estimated |

TABLE 2-continued

| Label | Equation | Description |
|---|---|---|
| 8 | $$FICO_{2,g1,B} = \frac{RR \cdot \left[\left(FETCO_{2,R} + \frac{10}{PB-47}\right)\left(FRC + \frac{\dot{V}_{g1}}{RR}\right) - FRC \cdot FETCO_{2,R}\right]}{\dot{V}_{g1}}$$ | Can be used to estimate the fractional concentration of $CO_2$ required the bolus breath to raise end-tidal $CO_2$ by about 10 mmHg from baseline |
| 9 | $\|FETCO_{2,T,x} - FETCO_{2,T,x-1}\| < \|FETCO_{2,T,x+1} - FETCO_{2,T,x}\|$ | Applied to each breath of the test to detect recirculation of the arterial blood |
| 3a2 | $\dot{Q}_{calc} = \dot{Q}_{est} + k(FETCO_{2,B} - FETCO_{2,T}) \; k > 0$ | An alternative to calculate cardiac output from an estimated cardiac output and the drift of end-tidal $CO_2$ observed during a test executed with said estimate |
| 3b2 | $C\bar{v}CO_{2,calc} = C\bar{v}CO_{2,est} - k(FETCO_{2,B} - FETCO_{2,T}) \; k > 0$ | An alternative to calculate mixed-venous $CO_2$ from an estimated mixed-venous $CO_2$ and the drift of end-tidal $CO_2$ observed during a test executed with said estimate |
| 4-O | $$\dot{V}CO_2 = \dot{V}_{g1} \cdot \underbrace{\frac{310}{293}}_{BTPS} \cdot [FETCO_2 - FICO_{2,g1}]$$ | An alternative, slightly less accurate, measure of minute volume of expired $CO_2$ than (4) when oxygen monitoring is not present. |
| 5-O | $\dot{V}_{g1} \cdot \frac{310}{293} \cdot [FETCO_2 - FICO_{2,g1}] = \dot{Q}(C\bar{v}CO_2 - CaCO_2)$ | Substitution of (4-O) for $\dot{V}CO_2$ in (1) |
| 6a-O | $$C\bar{v}CO_2 = \frac{\dot{V}_{g1} \cdot \frac{310}{293} \cdot [FETCO_2 - FICO_{2,g1}]}{\dot{Q}} + CaCO_2$$ | Rearrangement of (5-O) for the mixed-venous $CO_2$ where the end-tidal $CO_2$, the flow of gas to a sequential gas delivery circuit, the arterial $CO_2$ concentration, and cardiac output are known or estimated |
| 6b-O | $$\dot{Q} = \frac{\dot{V}_{g1} \cdot \frac{310}{293} \cdot [FETCO_2 - FICO_{2,g1}]}{C\bar{v}CO_2 - CaCO_2}$$ | Rearrangement of (5-O) for the cardiac output where the end-tidal $CO_2$, the flow of gas to a sequential gas delivery circuit, the arterial $CO_2$ concentration, and the mixed-venous $CO_2$ concentration are known or estimated |
| 7a-O | $$FICO_{2,g1} = FETCO_2 - \frac{\dot{Q}(C\bar{v}CO_2 - CaCO_2)}{\dot{V}_{g1} \cdot \frac{310}{293}}$$ | Rearrangement of (5-O) for the inspired fraction of $CO_2$ required to maintain end-tidal $CO_2$ at a steady state where the end-tidal $CO_2$, the flow of gas to a sequential gas delivery circuit, the arterial $CO_2$ concentration, the mixed-venous $CO_2$ concentration, and cardiac output are known or estimated |
| 7b-O | $$\dot{V}_{g1} = \frac{\dot{Q}(C\bar{v}CO_2 - CaCO_2)}{\frac{310}{293} \cdot \left[\left(\frac{1 - FICO_{2,g1} - FIO_{2,g1}}{1 - FETCO_2 - FETO_2}\right) \cdot FETCO_2 - FICO_{2,g1}\right]}$$ | Rearrangement of (5-O) for the G1 gas flow required to maintain end-tidal $CO_2$ at a steady state where the end-tidal $CO_2$, the fractional concentration of $CO_2$ in the G1 gas, the arterial $CO_2$ concentration, the mixed-venous $CO_2$ concentration, and cardiac output are known or estimated |

The term "reference end tidal concentration" is used to describe a value obtained by measurement which reflects an arterial blood concentration of the test gas preferably obtained prior to a recirculation time, preferably a value or one or more averaged values obtained closest in time to recirculation since this value may most usefully reflect a new steady state value achieved as a result of administering the test gas. In this connection, it is noteworthy that although the differential Fick equation is a steady state equation, using reference end tidal test gas concentrations obtained before a steady is reached does not prevent the adjusted test value for the iterated variable to be refined recursively. Therefore, the "reference end tidal concentration" is preferably at least a "surrogate steady state value" i.e. a value preferably obtained before a recirculation time that equals or sufficiently represents a steady state value to make the iterative process of meeting the test criterion useful in practice. To reduce the number of iterations required to determine pulmonary blood flow, the surrogate steady state value is preferably selected to be one value, or one or more averaged values, determined to be closest to a recirculation time—generally one or more among the last test values obtained prior to a recirculation. Equation 9 may be used at each breath to detect recirculation of the arterial blood.

The term "refined test value" is used to refer to a value for a iterated variable that is revised relative a previous test value. Since the invention contemplates that more than one iterated variable may be employed and since the iterated variables are mathematically interrelated the term refined test value should be understood to include a value indirectly derived from data related to a prior test value related to another iterated variable.

The reference to an iterated variable which is determined by pulmonary blood flow and from which pulmonary blood flow can be computed generally refers to a mixed venous test gas concentration. In contrast to carbon dioxide, with respect to test gases such as oxyacetylene, which are not produced or reliably consumed, the mixed venous blood concentration is equal to the arterial concentration at steady state and hence may not provide useful information about the pulmonary blood flow. In this case, the choice of iterated variable for iteration of a test value would be pulmonary blood flow. If pulmonary shunt is known total pulmonary blood flow can also be used to compute total cardiac output.

The term "gas delivery apparatus" means a device that can be controlled to control the rate of flow of the test gas into the circuit or set the concentration of the test gas into the inspiratory gas, and preferably both, for example a respiratory gas blender known to those skilled in the art, for example a gas blender with rapid flow controllers, optionally a gas blender capable of delivering accurate mixes of three gases into the circuit. The apparatus and gas mixes may of the type described in published WO 2007/02197. The key functionality of the apparatus is understood to serve the role of establishing (by administering test gas containing inspiratory gas) and maintaining a test concentration of test gas. The gas delivery apparatus may be operatively associated with suitable gas analyzers to measure fractional carbon dioxide and oxygen concentrations at the mouth. The apparatus is operatively associated with a control system for controlling the gas delivery apparatus. The control system demands the required output of the gas delivery apparatus to maintain a test concentration of test gas in the manner described above. The control system or the apparatus comprises the necessary controllers for this purpose as described above, for example for controlling rate of flow of inspiratory gas and optionally separate flow controllers for controlling the rate of flow of the sources gases.

The gas delivery apparatus comprises at least one input port for receiving a source which may be an inspiratory gas containing the test gas, at least one output port for connection to a breathing circuit and a flow controller for controlling the rate of flow of the inspiratory gas.

The flow controller optionally controls a gas delivery means.

The term "gas delivery means", abbreviated refers to specifically to hardware for delivering (e.g. releasing, where the source gas is under pressure) specific volumes of a source gas comprising or consisting of the test gas for inspiration by the patient, preferably a device that is adapted to output volumes of variable incremental size. The gas delivery means may be any known gas delivery device such as a gas injector, or a valve, for example, a proportional flow control valve.

Optionally, the gas delivery apparatus is a gas blender, for example, an apparatus that comprises a plurality of input ports for connection to a plurality of gas sources in order to blend different gases that make up the test gas containing gas, for example oxygen, air, nitrogen and a test gas. Optionally, carbon dioxide is the test gas. A flow controller optionally controls a proportional solenoid valve operatively associated with each gas source and optionally a separate flow controller and valve is employed to set the rate of flow of the blended gas into a breathing circuit. Input devices are used to set the rate of flow of gas into the breathing circuit and the concentration of the test gas in the gas provided to the subject.

According to one aspect the invention is directed to a computer program product which implements a method according to the invention. The computer program product comprises a non-transitory computer readable medium encoded with program code for controlling operation of gas delivery device, the program code including code for iteratively generating a series of test values of a iterated variable based on an iterative algorithm as described above in order to maintain a test concentration of test gas. The program code may comprise code for:

A) providing an inspired concentration of a test gas that defines a test concentration of the test gas in the subject's end tidal exhaled gas;
B) using an iterative algorithm to set the gas delivery apparatus to deliver, for at least one series of inspiratory cycles, a test gas that is computed to target the test concentration of the test gas based a test value of the iterated varable;
C) obtaining input comprising measurements of end tidal concentrations of test gas for expiratory cycles corresponding to the at least one series of inspiratory cycles;
D) using at least one measurement obtained in step C) as a reference end tidal concentration value to generate at least one of the following outputs:
   (1) the test value satisfies the test criterion;
   (2) a refined test value;
   wherein the reference end tidal concentration is a surrogate steady state value and the refined test value is ascertainable from the reference end tidal concentration;

The program code may include code to test a series of test values for the iterated varable based on the following criteria:

If output (1) is not obtained, repeating step (A) to (D) as necessary at least until output (1) is obtained; and If output (1) is obtained, outputting a value for pulmonary blood flow which, based on the test criterion, sufficiently represents a subject's true pulmonary blood flow.

As described above, the computer readable medium or computer readable memory has recorded thereon computer executable instructions for carrying out one or more embodiments of the above-identified methods. The invention is not limited by a particular physical memory format on which such instructions are recorded for access by a computer. Non-volatile memory exists in a number of physical forms including non-erasable and erasable types. Hard drives, DVDs/CDs and various types of flash memory may be mentioned. The invention, in one broad aspect, is directed to a non-transitory computer readable medium comprising computer executable instructions for carrying out one or more embodiments of the above-identified method.

The term "test concentration" means a concentration of a test gas in a subject's arterial blood as reflected in the end tidal concentration of the test gas in the subject's exhaled gas after attaining equilibrium with that arterial concentration of test gas. As described above, this concentration is optionally achieved by arranging for a subject to obtain an inspiratory gas with any suitable concentration of test gas which may be delivered via the gas delivery apparatus or optionally indirectly from a re-breathed gas.

The term "computer" is used broadly to refer to any device (constituted by one or any suitable combination of components) which may used in conjunction with discrete electronic components to perform the functions contemplated herein, including computing and obtaining input signals and providing output signals, and optionally storing data for computation, for example inputs/outputs to and from electronic components and application specific device components as contemplated herein. The computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from a gas analyzer, any type of input device for inputting inputs as contemplate herein (for example, a knob, dial, keyboard, keypad, mouse, touch screen etc.) input from a computer readable memory etc. Key outputs include output of a control signal to control to a gas delivery mean such as a proportional control valve, for example outputs to a flow controller for controlling key components of gas delivery apparatus.

It is to be understood that an iterative algorithm may execute computation based on a test mathematical relationship herein and that this relationships may be variously defined with equivalent formula in which terms/parameters are substituted by equivalent expressions that are expressed in other forms or styles e.g. read from a graph etc. Hence the invention is not limited by a reference to particular expressions of a test mathematical relationship or related equations. For example, equation 5 may expressed by equivalent expressions of equation 1 from which it is derived may be obtained by computing $\dot{V}CO_2$ (eq. 4) in a manner other than expressed in equation 4. It is understood that the equations relate back to the Fick equation and differential Fick equation and hence a iterative algorithm expressed as being "based on" the Fick equation" is understood to be encompass equivalent expressions or expansions of the equation with and without correction factors. In contrast to prior methods, in one embodiment of a method according to the invention, which is also primarily described hereafter in connection with using carbon dioxide as an embodiment of a "test gas", the invention contemplates obtaining steady state values optionally when the subject is at "rest" and those values are stabilized. $VCO_2$ and $CaCO_2$ are measured in a first steady state. Rather than waiting for end-tidal $CO_2$ to exponentially drift up to some second steady-value (which notably is generally not achieved before a recirculation), the present method contemplates giving a bolus of $CO_2$ to more acutely increase end-tidal $CO_2$ and calculate the inspired $CO_2$ required to force a second steady state at the elevated end-tidal $CO_2$ from a guess at the cardiac output. If the end-tidal $CO_2$ remains stable, the guess at cardiac output was correct. If the guess at cardiac output was incorrect, much like in the previous art, the end-tidal $CO_2$ will exponentially drift towards a steady state until recirculation. If we apply the differential Fick formula to our rest state and a second state represented for example by the last test breath before recirculation, it is possible to calculate a value for cardiac output. Much like previous methods, if the last test breath doesn't actually represent steady state (i.e. equilibration did not occur before recirculation), the cardiac output calculated by the differential Fick will be in error. However, it will be closer to the actual cardiac output than an original guess going in, and therefore, represents a refined estimate of the actual cardiac output. If this procedure is executed again, but with the refined estimate of cardiac output calculated from the last iteration, then there will be less drift during the test, the last test breath will better represent steady state, and again, our calculation of cardiac output will be even closer to the actual cardiac output. Repeat as necessary and the cardiac output calculated by this method will converge to the actual cardiac output. Accordingly, in contrast to prior methods there is no need to fit exponentials and extrapolate. In one embodiment, with sequential gas delivery (SGD), it is possible to clamp alveolar ventilation, and therefore measure a very consistent $VCO_2$ with equation 4 obviating the need for simultaneous flow/$CO_2$ measurements. To implement the test, an operator can provide a precise reduction in alveolar ventilation that will not be affected by changes in minute ventilation, and can therefore be used in spontaneous breathers and mechanically ventilated subjects.

Iterative NICO Equations

A method according to the invention will now be described in accordance with a preferred embodiment of the invention in which the test gas is carbon dioxide.

With the use of sequential gas delivery, alveolar ventilation can be controlled independent of overall minute ventilation. As a result, EQUATION 4 provides an accurate measure of the net minute volume of expired $CO_2$ calculated from the end-tidal fractional concentrations of $CO_2$ and $O_2$ ($FETCO_2$, $FETO_2$) without the use of breath collection or flowmetry.

EQUATION 4

$$\dot{V}CO_2 = \dot{V}_{g1} \cdot \underbrace{\frac{310}{293}}_{BTPS} \cdot \left[ \underbrace{\left( \frac{1 - FICO_{2,g1} - FIO_{2,g1}}{1 - FETCO_2 - FETO_2} \right)}_{Haldane} \cdot FETCO_2 - FICO_{2,g1} \right]$$

The correction term, BTPS, accounts for the expansion of gases in the lung owing to the increase in temperature from standard conditions. The Haldane term applies the Haldane transform to calculate the expired volume when only the inspired volume is known.

When the amount of $CO_2$ in the alveolar space is unchanging, EQUATION 4 can be substituted into EQUATION 1. The resulting steady state mass balance equation for the alveolar space is shown in EQUATION 5.

EQUATION 5

$$\dot{V}_{g1} \cdot \frac{310}{293} \cdot \left[ \left( \frac{1 - FICO_{2,g1} - FIO_{2,g1}}{1 - FETCO_2 - FETO_2} \right) \cdot FETCO_2 - FICO_{2,g1} \right] =$$
$$\dot{Q}(C\bar{v}CO_2 - CaCO_2)$$

Equation 5, based on the differential Fick equation, is a key test mathematical relationship from which other mathematical relationships are derived by solving for a test variable or an apparatus controllable variable.

The results of solving EQUATION 5 for the mixed-venous concentration of $CO_2$ and the pulmonary blood flow are shown in EQUATIONS 6.

$$C\bar{v}CO_2 = \qquad \text{EQUATION 6a}$$

$$\frac{\dot{V}_{g1} \cdot \frac{310}{293} \cdot \left[\left(\frac{1 - FICO_{2,g1} - FIO_{2,g1}}{1 - FETCO_2 - FETO_2}\right) \cdot FETCO_2 - FICO_{2,g1}\right]}{\dot{Q}} + CaCO_2$$

$$\text{EQUATION 6b}$$

$$\dot{Q} = \frac{\dot{V}_{g1} \cdot \frac{310}{293} \cdot \left[\left(\frac{1 - FICO_{2,g1} - FIO_{2,g1}}{1 - FETCO_2 - FETO_2}\right) \cdot FETCO_2 - FICO_{2,g1}\right]}{C\bar{v}CO_2 - CaCO_2}$$

Similarly, the results of solving EQUATION 5 for the fractional concentration of $CO_2$ in the G1 gas and the flow rate of G1 gas are shown in EQUATIONS 7.

$$FICO_{2,g1} = \frac{\dot{V}_{g1} \cdot \frac{310}{293} \cdot FETCO_2 \cdot (FIO_{2,g1} - 1) + \dot{Q}(C\bar{v}CO_2 - CaCO_2)(1 - FETO_2 - FETCO_2)}{\dot{V}_{g1} \cdot \frac{310}{293} \cdot (FETO_2 - 1)}$$

EQUATION 7a $$\dot{V}_{g1} = \frac{\dot{Q}(C\bar{v}CO_2 - CaCO_2)}{\frac{310}{293} \cdot \left[\left(\frac{1 - FICO_{2,g1} - FIO_{2,g1}}{1 - FETCO_2 - FETO_2}\right) \cdot FETCO_2 - FICO_{2,g1}\right]}$$

EQUATION 7b

The Iterative NICO Method

The partial pressure of $CO_2$ in the arterial blood is assumed to be equal to the end-tidal partial pressure of $CO_2$ and then converted to a concentration via the $CO_2$ dissociation curve of oxygenated whole blood [3,4]. This requires haemoglobin concentration ([HB]). [HB] is preferably obtained from a blood gas analysis. If blood gas analysis is not possible, [HB] can be measured transcutaneously. Alternatively, [HB] can be obtained from the normal published ranges for age/sex. End-tidal fractional concentrations can be converted to partial pressures by multiplying the fractional concentrations by barometric pressure (PB) less the partial pressure of water vapour.

The amount of $CO_2$ in the lung is entirely determined by the alveolar ventilation and the diffusion of $CO_2$ between the circulation and the alveolar space. If the pulmonary blood flow or the mixed-venous concentration of $CO_2$ is known, the other can be calculated from the steady state minute volume of expired $CO_2$ and arterial $CO_2$ concentration (EQUATIONS 6a,b). Therefore, the transfer rate of $CO_2$ between the circulation and the alveolar space can be determined for any value of end-tidal $CO_2$ as long as the pulmonary blood flow and mixed-venous concentration of $CO_2$ remains unchanged. Correspondingly, following an acute change in end-tidal $CO_2$ from a previously steady value, if the alveolar ventilation can be controlled or measured, a temporary steady state at the new end-tidal $CO_2$ (referred to as a test concentration) can be maintained by delivering the inspired fraction of $CO_2$ and/or alveolar ventilation required to exactly offset the influx from the circulation (EQUATIONS 7). This steady state can be maintained until the mixed-venous $CO_2$ changes due to recirculation of the affected arterial blood.

Our algorithm recursively exploits this observation to measure the pulmonary blood flow. According to one embodiment, throughout each iteration, the alveolar ventilation ($=\dot{V}_{g1}$) is set with a sequential gas delivery circuit. The fraction of $O_2$ in the G1 gas ($FIO_{2,g1}$) is not important, but should be held constant at a level sufficient to maintain arterial oxygen saturation. The end-tidal gases are measured by continuous real-time analysis of the expired gas.

In the baseline phase, the fractional concentration of $CO_2$ in the G1 gas ($FICO_{2,g1,R}$) is set and held constant. Although not necessary, $FICO_{2,g1,R}$ is usually zero. The G1 gas flow during the rest phase ($\dot{V}_{g1,R}$) is usually set to about 80% of the subjects total measured or estimated minute ventilation. In general, $\dot{V}_{g1,R}$ should be low enough to permit rebreathing which at least fills the subject's anatomical dead space, but high enough to prevent hypercapnia. The baseline phase can be ended when end-tidal $CO_2$ is stable. Stability of end-tidal $CO_2$ can be determined by the standard-deviation of end-tidal $CO_2$ measured over five breaths being within ±2 mmHg, or if the difference between the largest and smallest end-tidal $CO_2$ measured over the last 5 breaths is within ±2 mmHg, or if the slope of the linear regression line passing through the end-tidal $CO_2$ of the last five breaths is less than ±0.5 mmHg/breath. Alternatively, the baseline period can be ended after predefined time has elapsed and/or predefined number of breaths has occurred.

At the end of the baseline phase, the end-tidal $CO_2$ during the baseline phase ($FETCO_{2,R}$) is converted to an arterial concentration ($CaCO_{2,R}$). The end-tidal $CO_2$ from the last breath of the baseline phase can be used as $FETCO_{2,R}$. Alternatively, $FETCO_{2,R}$ can be the average of a number of breaths at the end of the baseline phase. The baseline minute volume of expired $CO_2$ ($\dot{V}CO_{2,R}$) is calculated from EQUATION 4, using the average end-tidal $O_2$ ($FETO_{2,R}$) measured during the baseline phase, $\dot{V}_{g1,R}$, $FICO_{2,g1,R}$, $FIO_{2,g1}$, and $FETCO_{2,R}$. A test value for an iterated variable, e.g. mixed-venous concentration of $CO_2$ is estimated from EQUATION 6a using an estimate of the pulmonary blood flow ($\dot{Q}_{est}$), $\dot{V}_{g1,R}$, $FICO_{2,g1,R}$, $FIO_{2,g1}$, $FETCO_{2,R}$, $FETO_{2,R}$, and $CaCO_{2,R}$. Alternatively, a test value for pulmonary blood flow (a preferred iterated variable for convenience) is estimated starting from an estimate of the mixed-venous concentration of $CO_2$ ($C\bar{v}CO_{2,est}$) using EQUATION 6b with $\dot{V}_{g1,R}$, $FICO_{2,g1,R}$, $FIO_{2,g1}$, $FETCO_{2,R}$, $FETO_{2,R}$, and $CaCO_{2,R}$.

To transition from the baseline phase to the test phase, the inspired fraction of $CO_2$ in the G1 gas is increased substantially for one bolus breath, inducing a sharp increase in the end-tidal $CO_2$. The bolus breath may optimally increase end-tidal $CO_2$ by approximately 10 mmHg to provide sufficient measurement resolution and minimize discomfort to the patient. The inspired fraction of $CO_2$ in the bolus breath ($FICO_{2,g1,B}$) required to elevate end-tidal $CO_2$ by approximately 10 mmHg can be calculated using an approximation of the subject's functional residual capacity (FRC), respiratory rate (RR), $\dot{V}_{g1,R}$, and $FETCO_{2,R}$ using EQUATION 8. The FRC can be estimated or obtained from normal published ranges for the age, weight, and sex of the subject. Respiratory rate can be measured or estimated. For most adults, $FICO_{2,g1,B}$ of 15-20% should provide an adequate increase in end-tidal $CO_2$.

EQUATION 8

$$FICO_{2,g1,B} = \frac{RR \cdot \left[\left(FETCO_{2,R} + \frac{10}{PB - 47}\right)\left(FRC + \frac{\dot{V}_{g1}}{RR}\right) - FRC \cdot FETCO_{2,R}\right]}{\dot{V}_{g1,R}}$$

The elevated end-tidal $CO_2$ (FETCO$_{2,B}$), and corresponding arterial $CO_2$ (CaCO$_{2,B}$) measured in the exhalation immediately following inspiration of the bolus are recorded. This recorded value represents the test concentration of CO2 sought to be maintained in the test phase. Subsequently, a value for an apparatus controllable variable preferably selected from the inspired fraction of $CO_2$ (FICO$_{2,g1,T}$) and G1 flow rate ($\dot{V}_{g1,T}$) during the test phase are set to try and maintain end-tidal $CO_2$ at FETCO$_{2,B}$. $\dot{V}_{g1,T}$ can be chosen arbitrarily, but in general, $\dot{V}_{g1,T}$ should be low enough to permit rebreathing which at least fills the subject's anatomical dead space. A test mathematical relationship solving for FICO2,g1 (EQUATION 7a), with $\dot{Q}_{est}$, $C\bar{v}CO_{2,est}$, $\dot{V}_{g1,T}$, FIO$_{2,g1}$, FETCO$_{2,B}$, FETO$_{2,R}$, and CaCO$_{2,B}$, can be used to calculate FICO$_{2,g1,T}$ presumed to force a second steady state of end-tidal $CO_2$ at FETCO$_{2,B}$. Alternatively, FICO$_{2,g1,T}$ can be set arbitrarily within the limitations of the hardware and the test mathematical relationship solves for Vg1 (EQUATION 7b), with $\dot{Q}_{est}$, $C\bar{v}CO_{2,est}$, FICO$_{2,g1,T}$, FIO$_{2,g1}$, FETCO$_{2,B}$, FETO$_{2,R}$, and CaCO$_{2,B}$, can be used to calculate $\dot{V}_{g1,T}$ presumed to force a second steady state of end-tidal $CO_2$ at FETCO$_{2,B}$. This $\dot{V}_{g1,T}$ and FICO$_{2,g1,T}$ is delivered until recirculation is detected (described later), or for a predefined length of time presumed to be less than the recirculation time, or a predefined number of breaths presumed to occur before recirculation.

At the end of the test phase, the end-tidal $CO_2$ during the test phase (FETCO$_{2,T}$) is converted to an arterial concentration (CaCO$_{2,T}$). The end-tidal $CO_2$ from the last breath of the test phase can be used as a reference end tidal concentration (FETCO2,T). Alternatively, FETCO$_{2,T}$ can be the average of values obtained for a number of breaths at the end of the test phase. The minute volume of expired $CO_2$ during the test phase ($\dot{V}CO_{2,T}$) is calculated from EQUATION 4, using the average end-tidal $O_2$ (FETO$_{2,T}$) measured during the test phase, $\dot{V}_{g1,T}$, FICO$_{2,g1,T}$, FIO$_{2,g1}$, and FETCO$_{2,T}$. Refined test values for pulmonary blood flow and mixed-venous $CO_2$ are recalculated ($\dot{Q}_{calc}$, $C\bar{v}CO_{2calc}$) from EQUATIONS 3a1,b1 using $\dot{V}CO_{2,R}$, CaCO$_{2,R}$, $\dot{V}CO_{2,T}$, and CaCO$_{2,T}$ or EQUATIONS 3a2,b2 using $\dot{Q}_{est}$, $C\bar{v}CO_{2,est}$, FETCO$_{2,B}$, and FETCO$_{2,T}$. Subsequently, the system is returned to the baseline state.

This manoeuvre is repeated within successively refined test values for the test variable utilizing either the calculated pulmonary blood flow of each test as the estimated pulmonary blood flow in the next iteration, or the calculated mixed-venous $CO_2$ concentration as the estimated mixed-venous $CO_2$ concentration in the next iteration.

Selecting the Apparatus Controllable Variable and its Values:

Although $\dot{V}_{g1,R}$ can be chosen arbitrarily, in general, $\dot{V}_{g1,R}$ should be low enough to permit rebreathing which at least fills the subject's anatomical dead space, but high enough to prevent hypercapnia. Although FICO$_{2,g1,R}$ can be chosen arbitrarily, in general, there is not often a reason to deliver $CO_2$ in the baseline phase, and FICO$_{2,g1,R}$ is generally set to zero. Although either $\dot{V}_{g1,T}$ or FICO$_{2,g1,T}$ can be set arbitrarily and the other value for the apparatus controllable variable calculated from EQUATIONS 7a,b, it is simplest to set $\dot{V}_{g1,T}$ equal to $\dot{V}_{g1,R}$ during the test phase and calculate FICO$_{2,g1,T}$ from EQUATION 7a.

No $O_2$

It is pertinent to note that knowledge of inspired and end-tidal $O_2$ is only required to implement the Haldane transform (EQUATION 4) which gives a measure of expired volumes when only inspired volumes are known. In practise, the expired volumes are not significantly different than inspired volumes. Where an oxygen analyzer is not present, the iterative algorithm method described herein can be executed with a small loss in accuracy using equations ending with (—O). (e.g. 7a-0, 7b-0, etc.)

Initiation and Convergence and Termination

The initial test value for the iterated variable, be it pulmonary blood flow or mixed-venous $CO_2$, is taken as the middle of the normal published range for the age, height, weight, and sex of the subject. Alternatively, the initial pulmonary blood flow or mixed-venous $CO_2$ estimate can be arbitrary. Alternatively, the test value for pulmonary blood flow can be estimated as 0.07 L/min/kg of subject body weight. Alternatively, the initial pulmonary blood flow or mixed-venous $CO_2$ estimate can be obtained from a pervious execution of the recursive algorithm. Alternatively, the initial test value for pulmonary blood flow or mixed-venous $CO_2$ can be obtained from another measurement technique (thermodilution, mixed-venous blood gases). Alternatively, the mixed-venous partial pressure of $CO_2$ can be estimated as 6 mmHg above the resting end-tidal $CO_2$ and converted to a concentration via the $CO_2$ dissociation curve.

If the test value for pulmonary blood flow does not satisfy the test criterion, the predicted transfer rate of $CO_2$ between the circulation and the alveolar space will also be in error. However, the minute volume of expired of $CO_2$ in the test phase will exponentially equilibrate with the flux across the blood-alveolar interface. As a result, the pulmonary blood flow calculated in each test will be refined and better reflect the actual pulmonary blood flow ($\dot{Q}_{est}$) than the ingoing test value. Because the iterative algorithm is implemented recursively, and the estimated test value for the iterative variable is refined after each iteration to reflect the previously calculated test values, the algorithm converges to the actual physiological parameters of the subject.

The rate at which the calculated parameters converge to the actual parameters depends on how fast the end-tidal $CO_2$ approaches equilibrium in the test phase. The derivative of an exponential function is largest at the start and vanishes with time. Therefore, a substantial refinement in the estimated parameters occurs in the breaths before recirculation. As a result, the calculated parameters at the end of each test are significantly more accurate than the previous estimates.

Testing is optionally terminated when the difference in pulmonary blood flow calculated between subsequent tests differs in magnitude less than a user-definable threshold. Optionally, the algorithm can be continued indefinitely. Optionally, the algorithm can be executed for a predefined number of iterations. All of these options satisfy a test criterion.

Detection of Recirculation

The pulmonary recirculation time varies between individuals, and within the same individual in different hemodynamic states. Indeed, the reported interval before recirculation occurs differs significantly amongst investigators.

We detect the occurrence of recirculation by analysis of the time course of the end-tidal $CO_2$ during the test phase. Prior to recirculation, the end-tidal $CO_2$ approaches a steady value exponentially—the absolute difference between consecutive end-tidal measurements decreases as the test proceeds. Recirculation causes a deviation from this asymptotic approach, detectable as an increase in the difference between consecutive end-tidal $CO_2$ measurements. Accordingly, in our method, the test proceeds as long as the magnitude of the difference between consecutive end-tidal $CO_2$ measurements is decreasing.

More specifically, let FETCO$_{2,T,x}$ be the end-tidal $CO_2$ of a breath during the test phase, and FETCO$_{2,T,x-1}$ and FETCO$_{2,T,x+1}$ be the breaths immediate before and after. The last breath before recirculation is the first test breath for which:

$$|FETCO_{2,T,x} - FETCO_{2,T,x-1}| < |FETCO_{2,T,x+1} - FETCO_{2,T,x}| \quad \text{EQUATION 9}$$

Apparatus

According to one embodiment of a gas delivery system, the system apparatus is shown in FIG. 1. It consists of a gas blender 22, a sequential gas delivery circuit 26, gas analyzers for oxygen 16 and carbon dioxide 18, a pressure transducer 14, a computer 8 including software 10 (which is optionally embodied a computer program product) that works the gas blender 22 to request gas flows and with the gas analyzers 16 and 18, pressure transducer 14 and input devices for measured or estimated physiological parameters 36 and algorithm settings 34 to obtain inputs as contemplated herein. The gas blender 22 may be connected to three pressurized gas tanks 32. The gas blender optionally contains three rapid flow controllers (not shown) capable of delivering accurate mixes of three source gases, optionally comprised of $CO_2$, $O_2$, and $N_2$ to the circuit. The concentrations of $CO_2$, $O_2$, and $N_2$ in the source gases must be such that they can produce the blends required to carry out the algorithm. Pure $CO_2$, $O_2$, and $N_2$ are one option. The gas analyzers 18 and 16 measure the fractional concentrations of $CO_2$ and $O_2$ at the mouth throughout the breath. The pressure transducer 14 is used for end-tidal detection. The computer runs a software implementation of a pulmonary blood flow measurement algorithm and demands the required mixtures from the blender 22. The monitor may display the real-time capnograph, oxigraph, pulmonary blood flow, and mixed-venous concentration of $CO_2$.

$$\dot{Q}_{calc} = \dot{Q}_{est} + k(FETCO_{2,B} - FETCO_{2,T})k > 0 \quad \text{EQUATION 3a2}$$

$$C\bar{v}CO_{2,calc} = C\bar{v}CO_{2,est} - k(FETCO_{2,B} - FETCO_{2,T})k > 0 \quad \text{EQUATION 3b2}$$

DESCRIPTION OF FIGURES

FIG. 4

1 The initial pulmonary blood flow or mixed-venous $CO_2$ estimate is taken as the middle of the normal published range for the age, height, weight, and sex of the subject. Alternatively, the initial pulmonary blood flow or mixed-venous $CO_2$ estimate can be arbitrary. Alternatively, pulmonary blood flow can be estimated as 0.07 L/min/kg of subject body weight. Alternatively, the initial pulmonary blood flow or mixed-venous $CO_2$ estimate can be obtained from a pervious execution of the recursive algorithm. Alternatively, the initial pulmonary blood flow or mixed-venous $CO_2$ estimate can be obtained from another measurement technique (thermodilution, mixed-venous blood gases). Alternatively, the mixed-venous partial pressure of $CO_2$ can be estimated as 6 mmHg above the resting end-tidal $CO_2$ and converted to a concentration via the $CO_2$ dissociation curve.

2 In the baseline phase, the fractional concentration of $CO_2$ in the G1 gas ($FICO_{2,g1,R}$) is set and held constant. Although not necessary, $FICO_{2,g1,R}$ is usually zero. The G1 gas flow during the rest phase ($\dot{V}_{g1,R}$) is usually set to about 80% of the subjects total measured or estimated minute ventilation. In general, $\dot{V}_{g1,R}$ should be low enough to permit rebreathing which at least fills the subject's anatomical dead space, but high enough to prevent hypercapnia.

3 The baseline phase can be ended when end-tidal $CO_2$ is stable. Stability of end-tidal $CO_2$ can be determined by the standard-deviation of end-tidal $CO_2$ measured over five breaths being within ±2 mmHg, or if the difference between the largest and smallest end-tidal $CO_2$ measured over the last 5 breaths is within ±2 mmHg, or if the slope of the linear regression line passing through the end-tidal $CO_2$ of the last five breaths is less than ±0.5 mmHg/breath. Alternatively, the baseline period can be ended after predefined time has elapsed and/or predefined number of breaths has occurred.

4 At the end of the baseline phase, the end-tidal $CO_2$ during the baseline phase ($FETCO_{2,R}$) is converted to an arterial concentration ($CaCO_{2,R}$). The end-tidal $CO_2$ from the last breath of the baseline phase can be used as $FETCO_{2,R}$. Alternatively, $FETCO_{2,R}$ can be the average of a number of breaths at the end of the baseline phase.

5 The baseline minute volume of expired $CO_2$ ($\dot{V}CO_{2,R}$) is calculated from EQUATION 4, using the average end-tidal $O_2$ ($FETO_{2,R}$) measured during the baseline phase, $\dot{V}_{g1,R}$, $FICO_{2,g1,R}$, $FIO_{2,g1}$, and $FETCO_{2,R}$.

6 The mixed-venous concentration of $CO_2$ is estimated from EQUATION 6a using an estimate of the pulmonary blood flow ($\dot{Q}_{est}$), $\dot{V}_{g1,R}$, $FICO_{2,g1,R}$, $FIO_{2,g1}$, $FETCO_{2,R}$, $FETO_{2,R}$, and $CaCO_{2,R}$. Alternatively, the pulmonary blood flow is estimated starting from an estimate of the mixed-venous concentration of $CO_2$ ($C\bar{v}CO_{2,est}$) using EQUATION 6b with $\dot{V}_{g1,R}$, $FICO_{2,g1,R}$, $FIO_{2,g1}$, $FETCO_{2,R}$, $FETO_{2,R}$, and $CaCO_{2,R}$.

7 To transition from the baseline phase to the test phase, the inspired fraction of $CO_2$ in the G1 gas is increased substantially for one bolus breath, inducing a sharp increase in the end-tidal $CO_2$. In one embodiment, the bolus breath increases end-tidal $CO_2$ by approximately 10 mmHg to provide sufficient measurement resolution and minimize discomfort to the patient. The inspired fraction of $CO_2$ in the bolus breath ($FICO_{2,g1,B}$) required to elevate end-tidal $CO_2$ by approximately 10 mmHg can be calculated using an approximation of the subject's functional residual capacity (FRC), respiratory rate (RR), $\dot{V}_{g1,R}$, and $FETCO_{2,R}$ using EQUATION 8. The FRC can be estimated or obtained from normal published ranges for the age, weight, and sex of the subject. Respiratory rate can be measured or estimated. For most adults, $FICO_{2,g1,B}$ of 15-20% should provide an adequate increase in end-tidal $CO_2$.

EQUATION 8

$$FICO_{2,g1,B} = \frac{RR \cdot \left[\left(FETCO_{2,R} + \frac{10}{PB-47}\right)\left(FRC + \frac{\dot{V}_{g1}}{RR}\right) - FRC \cdot FETCO_{2,R}\right]}{\dot{V}_{g1,R}}$$

8 The elevated end-tidal $CO_2$ ($FETCO_{2,B}$), and corresponding arterial $CO_2$ ($CaCO_{2,B}$) measured in the exhalation immediately following inspiration of the bolus are recorded. This recorded value represents the test concentration of $CO_2$ sought to be maintained in the test phase.

9 Subsequently, the inspired fraction of $CO_2$ ($FICO_{2,g1,T}$) and G1 flow rate ($\dot{V}_{g1,T}$) during the test phase are set to try and maintain end-tidal $CO_2$ at $FETCO_{2,B}$. $\dot{V}_{g1,T}$ can be chosen arbitrarily, but in general, $\dot{V}_{g1,T}$ should be low enough to permit rebreathing which at least fills the subject's anatomical dead space. EQUATION 7a, with $\dot{Q}_{est}$, $C\bar{v}CO_{2,est}$, $\dot{V}_{g1,T}$ $FIO_{2,g1}$, $FETCO_{2,B}$, $FETO_{2,R}$, and $CaCO_{2,B}$, can be used to calculate $FICO_{2,g1,T}$ presumed to force a second steady state of end-tidal $CO_2$ at $FETCO_{2,B}$. Alternatively, $FICO_{2,g1,T}$ can be set arbitrarily within the limitations of the hardware and EQUATION 7b, with $\dot{Q}_{est}$, $C\bar{v}CO_{2,est}$, $FICO_{2,g1,T}$, $FIO_{2,g1}$, $FETCO_{2,B}$, $FETO_{2,R}$, and $CaCO_{2,B}$, can be used to calculate $\dot{V}_{g1,T}$ presumed to force a second steady state of end-tidal $CO_2$ at $FETCO_{2,B}$.

10 This $\dot{V}_{g1,T}$ and $FICO_{2,g1,T}$ is delivered until recirculation is detected (described later), or for a predefined length of time presumed to be less than the recirculation time, or a predefined number of breaths presumed to occur before recirculation.

11 At the end of the test phase, the end-tidal $CO_2$ during the test phase ($FETCO_{2,T}$) is converted to an arterial concentration ($CaCO_{2,T}$). The end-tidal $CO_2$ from the last breath of the test phase can be used as $FETCO_{2,T}$. Alternatively, $FETCO_{2,T}$ can be the average of a number of breaths at the end of the test phase.

12 The minute volume of expired $CO_2$ during the test phase ($\dot{V}CO_{2,T}$) is calculated from EQUATION 4, using the average end-tidal $O_2$ ($FETO_{2,T}$) measured during the test phase, $\dot{V}_{g1,T}$, $FICO_{2,g1,T}$, $FIO_{2,g1}$, and $FETCO_{2,T}$. Pulmonary blood flow and mixed-venous $CO_2$ are recalculated ($\dot{Q}_{calc}$, $C\bar{v}CO_{2calc}$) from EQUATIONS 3a1,b1 using $\dot{V}CO_{2,R}$, $CaCO_{2,R}$, $\dot{V}CO_{2,T}$, and $CaCO_{2,T}$ or EQUATIONS 3a2,b2 using $\dot{Q}_{est}$, $C\bar{v}CO_{2,est}$, $FETCO_{2,B}$, and $FETCO_{2,T}$. Subsequently, the system is returned to the baseline state.

This manoeuvre is repeated utilizing either the calculated pulmonary blood flow of each test as the estimated pulmonary blood flow in the next iteration, or the calculated mixed-venous $CO_2$ concentration as the estimated mixed-venous $CO_2$ concentration in the next iteration.

13 Testing is terminated when the difference in pulmonary blood flow calculated between subsequent tests differs in magnitude less than a user-definable threshold. Optionally, the algorithm can be continued indefinitely. Optionally, the algorithm can be executed for a predefined number of iterations.

FIG. 1

According to one embodiment of a gas delivery system, the system apparatus is shown in FIG. 1. It consists of a gas blender 22, a sequential gas delivery circuit 26, gas analyzers for oxygen 16 and carbon dioxide 18, a pressure transducer 14, a computer 8 including software 10 (which is optionally embodied a computer program product) that works the gas blender 22 to request gas flows and with the gas analyzers 16 and 18, pressure transducer 14 and input devices for measured or estimated physiological parameters 36 and algorithm settings 34 to obtain inputs as contemplated herein. The gas blender 22 may be connected to three pressurized gas tanks 32. The gas blender optionally contains three rapid flow controllers (not shown) capable of delivering accurate mixes of three source gases, optionally comprised of $CO_2$, $O_2$, and $N_2$ to the circuit. The concentrations of $CO_2$, $O_2$, and $N_2$ in the source gases must be such that they can produce the blends required to carry out the algorithm. Pure $CO_2$, $O_2$, and $N_2$ are one option. The gas analyzers 18 and 16 measure the fractional concentrations of $CO_2$ and $O_2$ at the mouth throughout the breath. The pressure transducer 14 is used for end-tidal detection. The computer runs a software implementation of a pulmonary blood flow measurement algorithm and demands the required mixtures from the blender 22. The monitor may display the real-time capnograph, oxigraph, pulmonary blood flow, and mixed-venous concentration of $CO_2$.

Other inputs to the algorithm include an initial estimate of pulmonary blood flow or mixed-venous $CO_2$ 36, and termination criteria for the algorithm 34.

FIG. 5

Panel A

In FIG. 5a (Panel A), three iterations of the recursive algorithm showing convergence of the calculated pulmonary blood flow to the actual pulmonary blood flow starting from an incorrect estimate. As shown, if the estimated pulmonary blood flow is incorrect, the predicted transfer rate of $CO_2$ between the circulation and the alveolar space will also be in error. However, the minute volume of expired of $CO_2$ in the test phase will exponentially equilibrate with the flux across the blood-alveolar interface. As a result, the pulmonary blood flow calculated in each test will better reflect the actual pulmonary blood flow ($\dot{Q}_{act}$) than the ingoing estimate. Because this procedure is implemented recursively, and the estimated parameters updated after each iteration to reflect the previously calculated values, the algorithm converges to the actual physiological parameters of the subject.

The rate at which the calculated parameters converge to the actual parameters depends on how fast the end-tidal $CO_2$ approaches equilibrium in the test phase. The derivative of an exponential function is largest at the start and vanishes with time. Therefore, a substantial refinement in the estimated parameters occurs in the breaths before recirculation. As a result, the calculated parameters at the end of each test are significantly more accurate than the previous estimates.

Panel B

FIG. 5B (Panel B) shows that (a) if the estimate of pulmonary blood flow is higher than the actual pulmonary blood flow, the end-tidal $CO_2$ in the test phase drifts exponentially upwards; (b) if the estimate of pulmonary blood flow is lower than the actual pulmonary blood flow, the end-tidal $CO_2$ in the test phase drifts exponentially downwards; (c) if the estimate of pulmonary blood flow is approximately equal to than the actual pulmonary blood flow, the end-tidal $CO_2$ in the test phase remains constant. It also shows how recirculation may be detected by analysis of the time course of the end-tidal $CO_2$ during the test phase. Prior to recirculation, the end-tidal $CO_2$ approaches a steady value exponentially—the absolute difference between consecutive end-tidal measurements decreases as the test proceeds. Recirculation causes a deviation from this asymptotic approach, detectable as an increase in the difference between consecutive end-tidal $CO_2$ measurements. Mathematically, this is shown in equation 9.

REFERENCES

[1] Geerts B F, Aarts L P, Jansen J R. Methods in pharmacology: measurement of cardiac output. Br J Clin Pharmacol. 2011 March; 71(3):316-30.

[2] Fick A. Ueber die Messung des Blutquantums in den Herzventrikeln. Sitzungsberichte der Physiologisch-Medizinosche Gesellschaft zuWuerzburg 1870; 2: 16.

[3] Douglas A R, Jones N L, Reed J W. Calculation of whole blood CO2 content. J Appl Physiol. 1988 July; 65(1):473-7.

[4] Kelman R G. Digital computer procedure for the conversion of PCO2 into blood content. Respir Physiol 3: 111-115, 1967.

[5] DEFARES J G. Determination of PvCO2 from the exponential CO2 rise during rebreathing. J Appl Physiol. 1958 September; 13(2):159-64.

[6] COLLIER CR. Determination of mixed venous CO2 tensions by rebreathing. J Appl Physiol. 1956 July; 9(1): 25-9.

[7] Gedeon, A., Forslund, L., Hedenstierna, G., Romano, E. (1980). A new method for noninvasive bedside determination of pulmonary blood flow. Med Biol Eng Comput 18(4), 411-8.

[8] Jaffe M B. Partial CO2 rebreathing cardiac output—operating principles of the NICO system. J Clin Monit Comput. 1999 August; 15(6):387-401.

[9] Tachibana K, Imanaka H, Takeuchi M, Takauchi Y, Miyano H, Nishimura M. Noninvasive cardiac output measurement using partial carbon dioxide rebreathing is less accurate at settings of reduced minute ventilation and when spontaneous breathing is present. Anesthesiology. 2003 April; 98(4):830-7.

[10] Yem J S, Tang Y, Turner M J, Baker A B. Sources of error in noninvasive pulmonary blood flow measurements by partial rebreathing: a computer model study. Anesthesiology. 2003 April; 98(4):881-7.

[11] Somogyi R B, Vesely A E, Preiss D, Prisman E, Volgyesi G, Azami T, et al. Precise control of end-tidal carbon dioxide levels using sequential rebreathing circuits. Anaesth Intensive Care 2005 December; 33(6):726-32.

The invention claimed is:

1. A method of controlling a sequential gas delivery apparatus to deliver a test gas (TG) for non-invasively determining a subject's pulmonary blood flow comprising the steps of:
   (a) Using an iterative algorithm to control at least one apparatus controllable variable to test one or more test values for an iterated variable by:
      A) obtaining input of a steady state value of an end tidal test gas concentration and a corresponding value of at least one apparatus controllable variable for use in the iterative algorithm;
      B) providing an inspired concentration of a test gas over a first portion of an inspiratory cycle that achieves a test concentration of the test gas in the subject's end tidal exhaled gas and providing a neutral gas over a second portion of the respective inspiratory cycle to at least fill the subject's anatomical dead space;
      C) using a test value of the iterated variable in the iterative algorithm to set the sequential gas delivery apparatus to deliver, for at least one series of inspiratory cycles, an inspiratory gas comprising a test gas that is computed to maintain the test concentration of the test gas in the subject's end tidal exhaled gas;
      D) obtaining input comprising measurements of end tidal concentrations of test gas for expiratory cycles corresponding to the at least one series of inspiratory cycles and a corresponding value of at least one apparatus controllable variable for use in the iterative algorithm;
      E) using at least one measurement obtained in step D) as a reference end tidal concentration value to generate at least one of the following outputs:
         (1) the test value satisfies a test criterion;
         (2) a refined test value;
         wherein the reference end tidal concentration is a surrogate steady state value and the reference end tidal concentration is used to refine the test value;
   (b) If output (1) is not obtained, repeating step (a) as necessary at least until output (1) is obtained; and
   (c) If output (1) is obtained, outputting a value for pulmonary blood flow which, based on the test criterion, sufficiently represents a subject's true pulmonary blood flow.

2. A method according to claim 1, wherein the reference end tidal concentration is the last measurement obtained prior to a recirculation or an average of such last measurements.

3. A method according to claim 2, wherein the test gas is carbon dioxide.

4. A method according to claim 1, wherein the iterative algorithm is characterized in that it defines a mathematical relationship between the at least one apparatus controllable variable, the iterated variable and the end tidal concentration of test gas attained by setting the apparatus controllable variable, such that the iterative algorithm is determinative of whether iteration on the test value satisfies a test criterion or iteratively generates a progressively refined test value.

5. A method according to claim 1, wherein the iterative algorithm employs a test mathematical relationship based on the Fick equation.

6. A method according to claim 5, wherein the refined test value is ascertained based on the differential Fick equation.

7. A method according to claim 1, wherein the apparatus controllable variable is the inspired concentration of test gas in the inspiratory gas.

8. A method according to claim 1, wherein the apparatus controllable variable is rate of flow of test gas containing inspiratory gas into the circuit, where the rate of flow is determinative of the alveolar ventilation.

9. A method according to claim 1, wherein the iterated variable is selected from the group consisting of pulmonary blood flow, a variable determined by pulmonary flow from which pulmonary blood flow can be mathematically computed, and a mixed venous concentration of test gas.

10. A gas delivery system adapted to deliver a test gas (TG) for non-invasively determining a subject's pulmonary blood flow comprising:
   A sequential gas delivery apparatus;
   A control system for controlling the sequential gas delivery apparatus including at least one apparatus controllable variable to test one or more test values for an iterated variable, the control system comprising a computer for executing an iterative algorithm, the gas delivery system including means for:
      A) Obtaining input of a steady state value of an end tidal test gas concentration and a corresponding value of at least one apparatus controllable variable for use in the iterative algorithm;
      B) providing an inspired concentration of a test gas over a first portion of an inspiratory gas that achieves a test concentration of the test gas in the subject's end tidal exhaled gas and providing a neutral gas over a second portion of the respective inspiratory cycle to at least fill the subject's anatomical dead space;
      C) using a test value of the iterated variable in an iterative algorithm to set the sequential gas delivery apparatus to deliver, for at least one series of inspiratory cycles, an inspiratory gas comprising a test gas that is computed to maintain the test concentration of the test gas based on a test value of the iterated variable;
      D) obtaining input comprising measurements of end tidal concentrations of test gas for expiratory cycles corresponding to the at least one series of inspiratory cycles;
      E) using at least one measurement obtained in step C) as a reference end tidal concentration value to generate at least one of the following outputs:

(1) the test value satisfies the test criterion;

(2) a refined test value;

wherein the reference end tidal concentration is a surrogate steady state value and is used to generate the refined test value;

wherein the iterative algorithm uses at least one apparatus controllable variable to iteratively test one or more of test values for the iterated variable based on the following criteria:

If output (1) is not obtained, repeating steps (B) to (E) as necessary at least until output (1) is obtained; and If output (1) is obtained, outputting a value for pulmonary blood flow which, based on the test criterion, sufficiently represents a subject's true pulmonary blood flow.

11. A gas delivery system according to claim 10, wherein the sequential gas delivery apparatus comprises at least one input port for receiving an inspiratory gas containing the test gas, at least one output port for connection to a breathing circuit and a flow controller for controlling the rate of flow of the inspiratory gas.

12. A gas delivery system according to claim 10, wherein the computer is CPU.

13. A gas delivery system according to claim 10, wherein reference end tidal concentration is the last measurement obtained prior to a recirculation or an average of such last measurements.

14. A gas delivery system according to claim 10, wherein the test gas is carbon dioxide.

15. A gas delivery system according to claim 10, wherein the iterative algorithm is characterized in that it defines a mathematical relationship between the at least one apparatus controllable variable, the iterated variable and the end tidal concentration of test gas attained by setting the apparatus controllable variable, such that the iterative algorithm is determinative of whether iteration on the test value satisfies a test criterion or iteratively generates a progressively refined test value.

16. A gas delivery system according to claim 15, wherein the iterative algorithm employs a test mathematical relationship based on the Fick equation.

17. A gas delivery system according to claim 10, wherein the apparatus controllable variable is the inspired concentration of test gas in the inspiratory gas.

18. A gas delivery system according to claim 10, wherein the apparatus controllable variable is rate of flow of test gas containing inspiratory gas into the circuit, where the rate of flow is determinative of the alveolar ventilation.

19. A method according to claim 10, wherein the iterated variable is selected from the group consisting of pulmonary blood flow, a variable determined by pulmonary flow from which pulmonary blood flow can be mathematically computed, and a mixed venous concentration of test gas.

20. A computer program product comprising a non-transitory computer readable medium encoded with program code for controlling the operation of a sequential gas delivery apparatus including at least one apparatus controllable variable, the program code including code for iteratively generating and evaluating test values of an iterated variable based on an iterative algorithm in order to output a test value of the iterated variable that meets a test criterion including program code for:

A) Obtaining input of a steady state value of an end tidal test gas concentration and a corresponding value of at least one apparatus controllable variable for use in the iterative algorithm;

B) providing an inspired concentration of a test gas over a first portion of an inspiratory cycle that achieves a test concentration of the test gas in the subject's end tidal exhaled gas and using the test value of the iterated variable in the iterative algorithm to set the sequential gas delivery apparatus to deliver, for at least one series of inspiratory cycles, an inspiratory gas comprising a test gas that is computed to maintain the test concentration of the test gas and providing a neutral gas over a second portion of the respective inspiratory cycle to at least fill the subject's anatomical dead space;

C) obtaining input comprising measurements of end tidal concentrations of test gas for expiratory cycles corresponding to the at least one series of inspiratory cycles;

D) using at least one measurement obtained in step C) as a reference end tidal concentration value to generate at least one of the following outputs:

(1) the test value satisfies the test criterion;

(2) a refined test value;

wherein the reference end tidal concentration is a surrogate steady state value and is used to obtain the refined test value;

wherein the iterative algorithm uses at least one apparatus controllable variable to iteratively test one or more of test values for the iterated variable based on the following criteria:

If output (1) is not obtained, repeating step (B) to (D) as necessary at least until output (1) is obtained; and If output (1) is obtained, outputting a value for pulmonary blood flow which, based on the test criterion, sufficiently represents a subject's true pulmonary blood flow.

* * * * *